US010082598B2

(12) United States Patent
Jernigan (10) Patent No.: US 10,082,598 B2
(45) Date of Patent: Sep. 25, 2018

(54) SENSOR POWER MANAGEMENT (71) Applicant: INTEL CORPORATION, Santa Clara, CA (US)

(72) Inventor: Charles Carter Jernigan, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 794 days.

(21) Appl. No.: 14/462,393

(22) Filed: Aug. 18, 2014

(65) Prior Publication Data

US 2016/0047679 A1    Feb. 18, 2016

(51) Int. Cl.
*G01N 19/10* (2006.01)
*G01D 3/10* (2006.01)
(Continued)

(52) U.S. Cl.
CPC ........... *G01V 8/00* (2013.01); *G01D 3/10* (2013.01); *G01L 9/00* (2013.01); *G01N 19/10* (2013.01);
(Continued)

(58) Field of Classification Search
CPC ........ G01C 19/00; G01C 17/00; G01N 19/10; G01D 3/10; G01V 8/00; G01P 15/0802; G01L 9/00
See application file for complete search history.

(56) References Cited

U.S. PATENT DOCUMENTS

2008/0125820 A1    5/2008  Stahmann
2010/0057044 A1*   3/2010  Hayter .............. A61M 5/14244
                                                        604/504
(Continued)

FOREIGN PATENT DOCUMENTS

CN    103080702 A    5/2013
CN    103250117 A    8/2013
(Continued)

OTHER PUBLICATIONS

Tompkins, et al., Biomedical Digital Signal Processing C-Language Examnples and Laboratory Experiments for the IBM PC, 2000, Prentice Hall, pp. 1-378.*
(Continued)

*Primary Examiner* — Roy Y Yi
*Assistant Examiner* — Lynne Anderson
(74) *Attorney, Agent, or Firm* — Schwabe, Williamson & Wyatt, P.C.

(57) ABSTRACT

Embodiments of the present disclosure provide techniques and configurations for an apparatus to reduce sensor power consumption, in particular, through predictive data measurements by one or more sensors. In one instance, the apparatus may include one or more sensors and a sensor management module coupled with the sensors and configured to cause the sensors to initiate measurements of data indicative of a process in a first data measurement mode, determine a pattern of events comprising the process based on a portion of the measurements collected by the sensors in the first data measurement mode over a time period, and initiate measurements of the data by the one or more sensors in a second data measurement mode. The second data measurement mode may be based on the pattern of events comprising the process. The pattern may indicate a prediction of appearance of events in the process. Other embodiments may be described and/or claimed.

13 Claims, 8 Drawing Sheets

(51) Int. Cl.
    *G01V 8/00*     (2006.01)
    *G01L 9/00*     (2006.01)
    *G01P 15/08*     (2006.01)
    *G01C 19/00*     (2013.01)
    *G01C 17/00*     (2006.01)

(52) U.S. Cl.
    CPC .......... *G01P 15/0802* (2013.01); *G01C 17/00* (2013.01); *G01C 19/00* (2013.01)

(56) References Cited

U.S. PATENT DOCUMENTS

| | | |
|---|---|---|
| 2010/0097259 A1 | 4/2010 | Zhang |
| 2010/0177037 A1 | 7/2010 | Kim et al. |
| 2011/0066053 A1* | 3/2011 | Yazicioglu ............ A61B 5/0428 600/509 |
| 2012/0004881 A1 | 1/2012 | Jung et al. |
| 2013/0140910 A1 | 6/2013 | Imai et al. |
| 2013/0198531 A1* | 8/2013 | Hansen .................... A61N 1/08 713/300 |
| 2014/0075055 A1 | 3/2014 | Yi et al. |
| 2014/0187264 A1 | 7/2014 | Min et al. |

FOREIGN PATENT DOCUMENTS

| | | |
|---|---|---|
| JP | 2004-355164 A | 12/2004 |
| JP | 2006-187316 A | 7/2006 |
| JP | 2006329677 A | 12/2006 |
| TW | 201250452 A | 12/2012 |
| TW | 201416971 A | 5/2014 |

OTHER PUBLICATIONS

International Search Report and Written Opinion dated Sep. 11, 2015, issued in corresponding International Application No. PCT/US2015/034943, 11 pages.

Office Action in Primary Examination dated Jan. 19, 2017, issued in Taiwan Patent Application No. 104122561, 5 pages.

International Preliminary Report on Patentability, dated Mar. 2, 2017, issued in corresponding International Application No. PCT/US2015/034943, 8 pages.

Notice of Reason(s) for Rejection dated Feb. 20, 2018, issued in Japanese Patent Application No. 2017-509624, 15 pages.

Extended Supplementary European Search Report, dated Mar. 9, 2018, issued in European Patent Application No. 15833677.6, 14 pages.

* cited by examiner

SENSOR POWER MANAGEMENT

FIELD

Embodiments of the present disclosure generally relate to the field of sensor devices, and more particularly, to managing sensing devices to save power.

BACKGROUND

There is a variety of different types of sensors, including accelerometers, gyroscopes, barometers, infrared proximity sensors, visible light sensors, microphones, compasses, thermometers, moisture sensors, etc. Such sensors typically capture raw data, which may then be interpreted. Different sensor types consume different amounts of power. Power management for sensors may include different methods. However, currently employed methods of sensor power management may not always be sufficient to reduce sensor power consumption to a desired level.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings.

DETAILED DESCRIPTION

Embodiments of the present disclosure include techniques and configurations to reduce sensor power consumption, in particular, through predictive data measurements by one or more sensors. In accordance with embodiments, an apparatus may include one or more sensors and sensor management modules coupled with the sensors and configured to cause the sensors to initiate measurements of data indicative of a process in a first data measurement mode, determine a pattern of events comprising the process based on a portion of the measurements collected by the sensors in the first data measurement mode over a time period, and initiate measurements of the data by the one or more sensors in a second data measurement mode. The second mode may be based on the pattern of events comprising the process. The pattern may indicate a prediction of appearance of events in the process. The first data measurement mode may include performing data measurements by the sensors at a first (e.g., fixed or variable) sampling rate.

The second data measurement mode may include performing the data measurements at a second sampling rate that is lower than the first sampling rate, performing the data measurements at a third sampling rate during periods of time corresponding to predicted appearances of events according to the determined pattern, or performing the data measurements at a fourth sampling rate during periods of time between predicted appearances of consecutive events in the process and performing the data measurements at a fifth sampling rate during the periods of time corresponding to predicted appearances of events. The fifth sampling rate may be greater than the fourth sampling rate. In some embodiments, the fifth sampling rate may be slower than the fourth sampling rate.

In the following detailed description, reference is made to the accompanying drawings that form a part hereof, wherein like numerals designate like parts throughout, and in which are shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical, electrical, or optical contact. However, "coupled" may also mean that two or more elements indirectly contact each other, but yet still cooperate or interact with each other, and may mean that one or more other elements are coupled or connected between the elements that are said to be coupled with each other.

Figure 1:
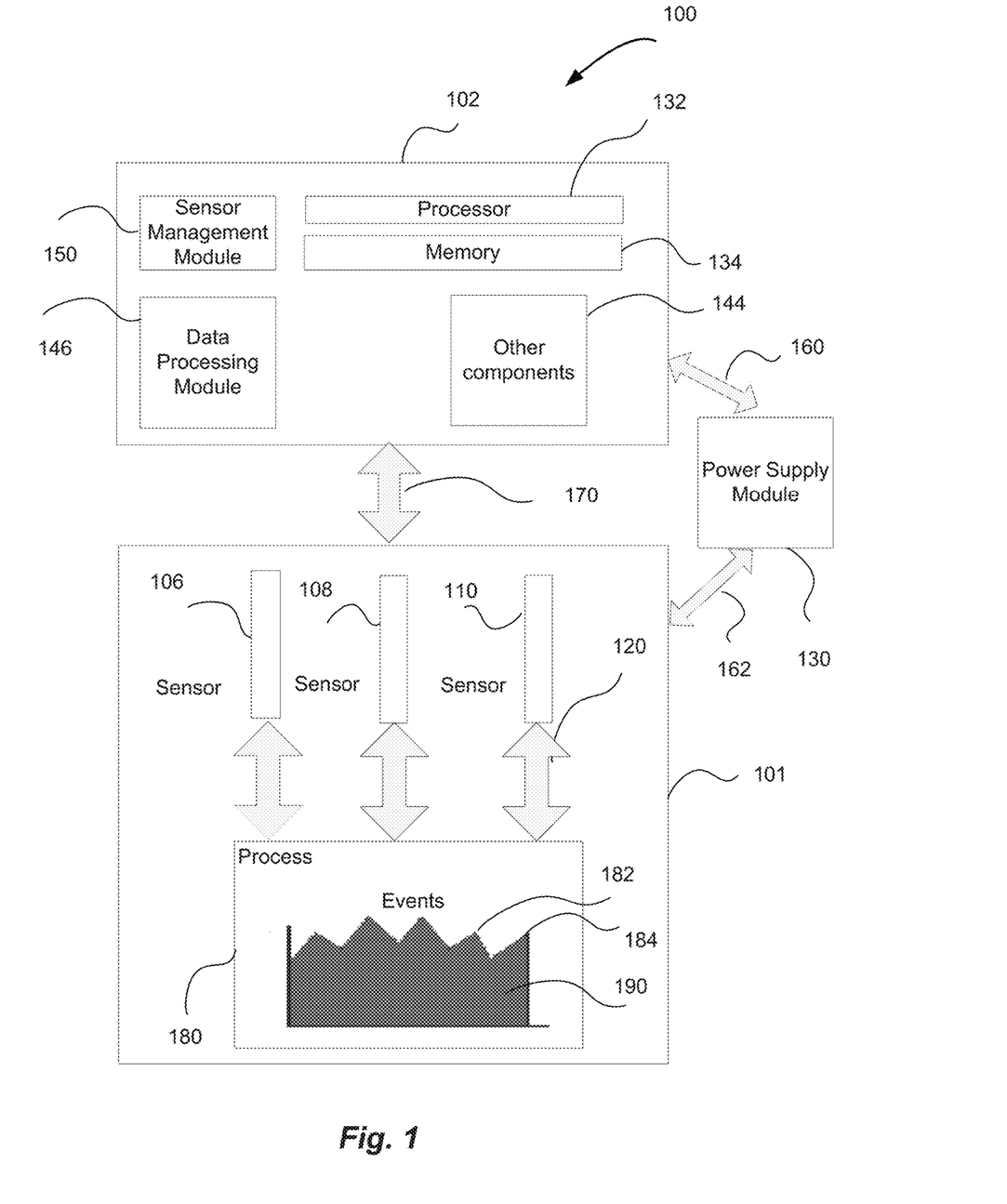
FIG. 1 schematically illustrates an example system for managing data measurements by one or more sensors in accordance with some embodiments of the present disclosure.

FIG. 1 schematically illustrates an example system 100 for managing data measurements by one or more sensors in accordance with some embodiments of the present disclosure. The system 100 may be used in various implementations. For example, the system 100 may comprise a wearable device configured to provide sensor measurement of data related to a user's activities. In another example, the system 100 may comprise a sensing device control system configured to manage multiple sensors to measure data related to a particular physical, chemical, biological, biometric, or other process.

In some embodiments, the system 100 may comprise a computing device 102 configured to manage a sensor module 101 that may include one or more sensors 106, 108, 110 (in some embodiments, a sensor array). The sensor module 101 may be communicatively coupled 170 with the computing device 102. The computing device 102 may include a processor 132 configured to manage the sensors 106, 108, 110 and to process data measured by the sensors and provided to the computing device 102. More specifically, the computing device 102 may include memory 134 having instructions (e.g., compiled in a sensor management module 150) that, when executed on the processor 132, may cause the processor 132 to perform sensor management operations adapted to save power consumed by the sensors 106, 108, 110 during the data measurement process.

For example, the sensor management module 150 may be configured to control power supply to the sensors 106, 108, 110 provided by a power supply module 130. The power supply module 130 may include a power source coupled 160, 162 with the computing device 102 and sensors 106, 108, 110 and configured to supply power to at least some (or all) of the sensors 106, 108, 110. The sensor management module 150 may manage powering on and off the sensors 106, 108, 110 by the power supply module 130.

In some embodiments, at least some of the sensors 106, 108, 110 may include a power supply source (e.g., built in or operatively coupled with the sensor(s)), such as a battery, which may be controlled (e.g., turned on and off) by the sensor management module 150.

Memory 134 may further include instructions (e.g., compiled in a data processing module 146) that, when executed on the processor 132, may cause the processor 132 to perform data processing of the data measured by the sensors 106, 108, 110.

The computing device 102 may include other components 144 necessary for the functioning of the computing device 102. For example, the computing device 102 may include a display (not shown) configured to display at least the results of the data measurements by the sensors 106, 108, 110, which may be provided by the execution of the module 146. The processor 132, memory 134, and other components 144 of the computing device 102 may be coupled with one or more interfaces (not shown) configured to facilitate information exchange among the above-mentioned components. Communications interface(s) (not shown) may provide an interface for the computing device 102 to communicate over one or more wired or wireless network(s) and/or with any other suitable device. An example configuration of the system 100 including the computing device 102 is described in greater detail in reference to FIG. 8.

As discussed, the sensor management module 150 and data processing module 146 may be implemented as a software component stored, e.g., in the memory 134 and configured to execute on the processor 132. In some embodiments, the sensor management module 150 and data processing module 146 may be implemented as a combination of software and hardware components. In some embodiments, the sensor management module 150 and data processing module 146 may include a hardware implementation.

As described above, the sensor module 101 may include sensors (e.g., sensor array) 106, 108, 110 operatively coupled 120 with a process 180 and configured to measure data indicative of the process 180. The sensors 106, 108, 110 are shown in FIG. 1 for illustrative purposes only; it will be appreciated that any number of sensors (e.g., one or more) may be used in the sensor module 101.

Generally, the process 180 may be any type of digital or analog process, continuous or periodic, that may be defined in measurable physical quantities, which may be convertible into a signal readable by a respective sensing device. Examples of measurable processes may include, but are not limited to, light, various types of motion, temperature, magnetic fields, gravity, humidity, moisture, vibration, pressure, electrical fields, sound, and other physical aspects of the external or internal environment. Other examples may include chemical composition of a matter or environment, biometric processes, and the like. The measurable data indicative of a process may include different physical characteristics and parameters. Accordingly, sensors 106, 108, 110 may include different types of sensors, including, but not limited to, accelerometers, gyroscopes, barometers, infrared proximity sensors, visible light sensors, transducers, actuators, and the like.

The process 180 may comprise events 182, 184, which may be indicative of the process 180. For example, a user's heartbeats may be considered events of the user's heart activity and may be measurable by a respective sensing device (e.g., heart rate monitor). The events 182, 184 comprising the process 180 may be of particular interest because the process 180 may be defined or otherwise understood by interpreting the events comprising the process and measured by the sensors 106, 108, 110. Referring to FIG. 1, the events 182, 184 represented as peaks of a graph 190 depicting the process 180 may be indicative of the process 180. Accordingly, the sensors 106, 108, 110 may be configured to perform measurements of the graph 190 values, including values representing events 182, 184 to obtain indications of the process 180, in accordance with embodiments described herein. (While only two events 182, 184 are illustrated in the process 180 for simplicity purposes, it will be understood that the process 180 may comprise multiple events similar to 182, 184.)

At least some measurable processes (e.g., process 180) may include events (e.g., events 182, 184) that may occur at substantially regular intervals. For example, a user's heartbeats or walking (running) steps may occur at regular intervals, e.g., with substantial periodicity. Accordingly, a pattern associated with such a process may be determined that may indicate a prediction of occurrence (appearance) of events in the process. The pattern associated with a process may be identified (e.g., derived from data indicative of the process) using a number of process data measurements accumulated over a period of time. After the pattern is identified, e.g., appearance of process events occurring at substantially regular intervals is predicted from the collected data, the pattern (e.g., appearance of process events as predicted) may be continuously verified, using the techniques described herein.

Figure 2:
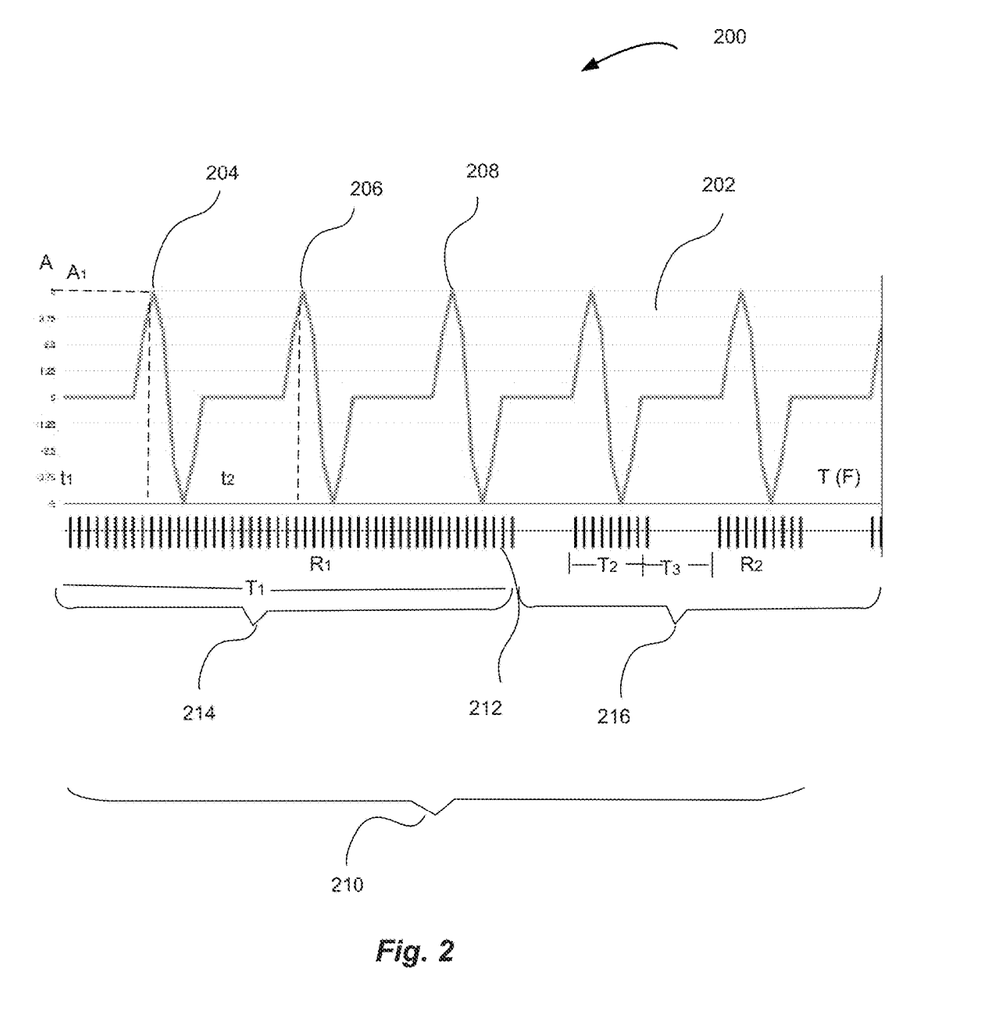
FIG. 2 is a schematic representation of an example predictive data measurement performance technique, using one or more sensors for data measurements of a process, according to some embodiments.

FIG. 2 is a schematic representation 200 of an example predictive data measurement performance technique, using one or more sensors for data measurements of a process, according to some embodiments. The process may be implemented using, for example, components described in reference to FIG. 1, for example, the sensor management module 150 and data processing module 146, and sensors 106, 108, 110.

The representation 200 may include a process 202 to be measured by the one or more sensors. As shown, the process 202 may comprise multiple events 204, 206, 208 . . . that may occur with substantial regularity (e.g., at substantially regular time intervals). The X axis of the process 202 may indicate duration (e.g., time T) or frequency of events appearance (e.g., F) of the process 202, while the Y axis may indicate amplitude value A associated with the process 202. The process data measurements 210 using the sensors 106, 108, 110 are schematically depicted by multiple vertical lines 212 placed along the X axis with determined intervals (hereinafter "rate"). Each line 212 may indicate an instance of measurement of the process 202 performed by at least one of the sensors 106, 108, or 110. As briefly discussed above, a conventional measurement technique that may be applied to the process 202 may include performing the data measurements at a fixed sampling rate, e.g., at fixed intervals or time periods.

In contrast, the measurements 210 illustrated in FIG. 2 may occur using at least two data measurement modes. For example, the measurements 210 of data indicative of the process 202 may be initiated by the one or more sensors in a first data measurement mode 214. The first data measurement mode 214 may comprise causing, by the sensor management module 150, the sensors 106, 108, 110 to perform the data measurements at a first sampling (e.g., fixed) rate $R_1$, for example, every few seconds. It will be understood that causing the sensors 106, 108, 110 to perform the data measurements may commence by causing, by the sensor management module 150, the sensors 106, 108, 110 to power on.

The sensor management module 150 and/or data processing module 146 may determine a pattern of events comprising the process 202, based at least on a portion of the measurements collected by the one or more sensors 106, 108, 110 in the first data measurement mode 214 over a time period $T_1$ as shown in FIG. 2. For example, determination of a pattern of events comprising the process 202 may include identifying data points $A_1$ (e.g., corresponding to events 204, 206, 208, and so on) and time instances, e.g., $t_1$, $t_2$, and so on (or corresponding time intervals or frequencies) approximately at which the identified data points are to be measured by the one or more sensors 106, 108, 110. Generally, a pattern may indicate a prediction of appearance of data points indicative of a process, at particular time intervals, with the desired margin of error.

After the pattern (e.g., a prediction of appearance of events 204, 206, 208 in the process 202) is determined, the sensor management module 150 may initiate measurements of the data of the process 202 by the one or more sensors 106, 108, 110 in a second data measurement mode 216, based on the determined pattern of events 204, 206, 208 comprising the process 202. More specifically, the sensor management module 150 may cause the sensors 106, 108, 110 to perform the data measurements at a second (e.g., fixed or continuously or otherwise varied) sampling rate $R_2$ during periods of time $T_2$ corresponding to predicted appearances of events 204, 206, 208 according to the determined pattern, e.g., at time instances $t_1$, $t_2$, etc. (It will be understood that the time instances of appearance of events 204, 206, 208 may occur within the periods of time $T_2$.)

If the data points corresponding to the predicted appearance of events 204, 206, 208, when measured, match the identified data points within a desired margin of error, a conclusion may be made that the pattern of events, as defined, correctly (e.g., within the margin of error) describes the process 202. Accordingly, the second data measurement mode 216 may comprise periodic verification of the pattern of events 204, 206, 208, as determined during the first data measurement mode 214.

Conversely, in the second data measurement mode 216, the sensor management module 150 may cause the sensors 106, 108, 110 to refrain from performing the data measurements during periods of time $T_3$ corresponding to intervals between the predicted appearances of events 204, 206, 208 according to the determined pattern. In some embodiments, the first sampling rate $R_1$ corresponding to the first data measurement mode 214 may not be the same as the second sampling rate $R_2$ corresponding to the second data measurement mode 216.

During the data measurements in the second data measurement mode 216, the sensor management module 150 and/or the data processing module 146 may determine, from the data being measured in the second mode, that the measured data points corresponding to the events 204, 206, 208 no longer match the determined pattern. For example, the values of the measured data points may no longer match the values of the identified data points $A_1$ within a desired margin of error (e.g., first margin). In another example, the times or frequencies of the appearance of the events may no longer match the predicted events' appearance times or frequencies within a desired margin of error (e.g., second margin).

In general, a result of matching the measured events to the pattern during the second data measurement mode 216 may exceed a desired margin of error. Accordingly, it may be determined that the pattern of events identified during the first data measurement mode 214 is no longer verifiable, e.g., it no longer correctly predicts the appearance of events 204, 206, 208 comprising the process 202. Based on this determination, the sensor management module 150 may revert to the first data measurement mode 214 of data measurements, in order to determine a new pattern, if any. If no new pattern is identified, e.g., after a period of time $T_1$, the sensors 106, 108, 110 may continue to perform data measurements in the first data measurement mode 214.

It will be understood that the total number of measurements 210 in the first and second data measurement modes 214 and 216 may be less than a number of measurements that may occur when performing the data measurements at a fixed sampling rate, during the same time period. Accordingly, the power consumption by the sensors 106, 108, 110 when utilizing the techniques described above may be reduced relative to the power consumption by the sensors 106, 108, 110 when performing the data measurements at the fixed sampling rate. The amount of saved power may depend on the rates of data measurements in the first and second data measurement modes 214 and 216.

It is important to note that the sample rate (e.g., used in the second data measurement mode 216) may be fixed (e.g., regular) or varied (e.g., irregular). For example, the sample rate may comprise taking 20 samples in 1 second and having the spacing between the samples variable. E.g., two consecutive sampling rates may be $\frac{1}{100}$ seconds apart, then $\frac{1}{10}$ seconds apart, and so on.

In another example, sampling rate may vary, e.g., in a continuous or aperiodic manner. For example, a sampling rate may vary over time as some sort of function. For example, the sampling rate may increase (e.g., have the highest value) around a point of interest corresponding to data points $A_1$ of predicted appearances of events 204, 206, 208, and decrease gradually toward halfway between points of interest. In other words, leading up to a point of interest, the sampling rate may get faster (higher). Moving away from a point of interest, the sampling rate may get slower (lower).

Figure 3:
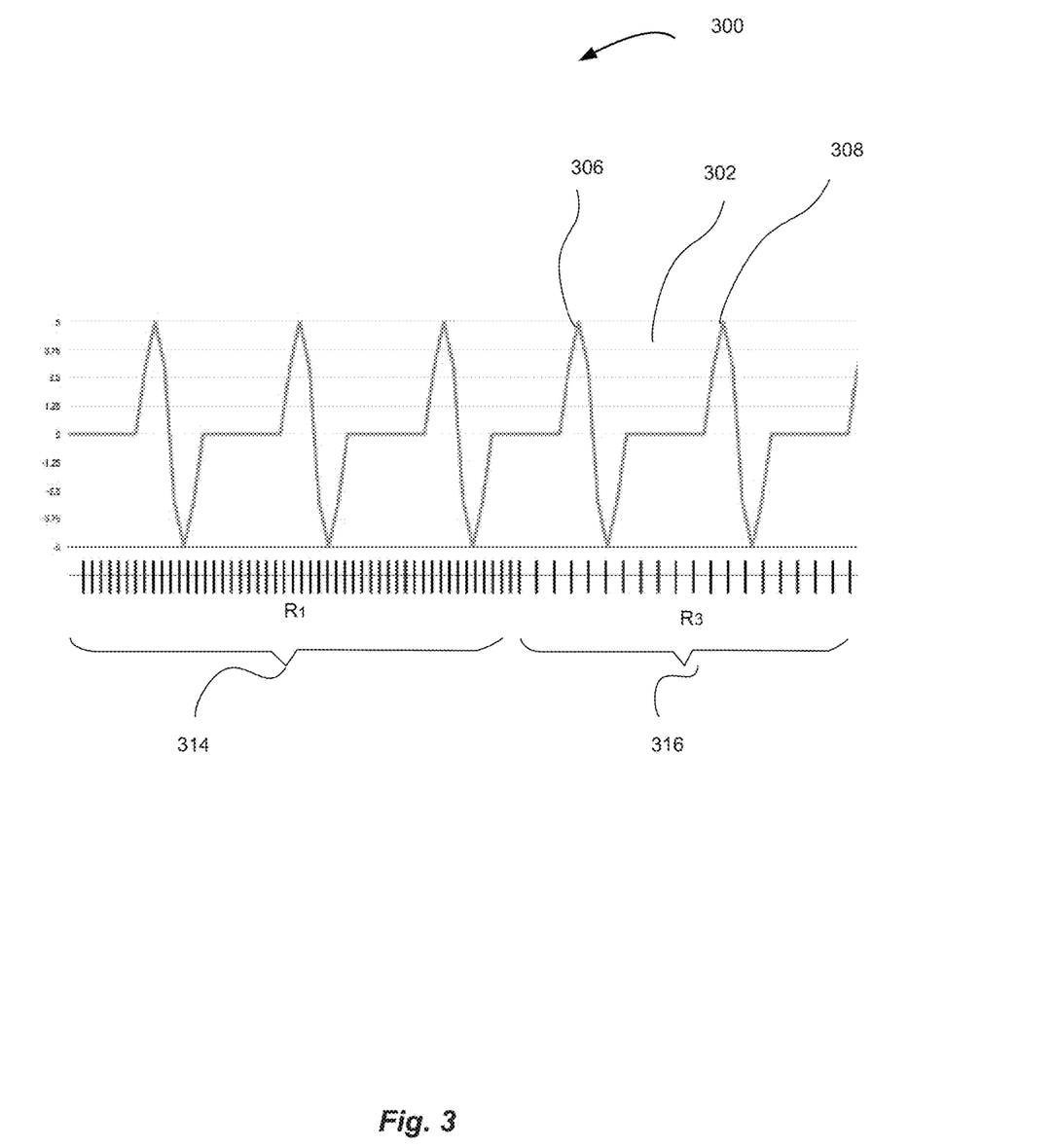
FIG. 3 is a schematic representation of another example predictive data measurement performance technique, using one or more sensors for data measurements of a process, according to some embodiments.

FIG. 3 is a schematic representation 300 of another example predictive data measurement performance technique, using one or more sensors for data measurements of a process, according to some embodiments. Similarly to the technique described in reference to FIG. 2, data measurements of a process 302 may be initially performed in a first data measurement mode 314, similar to 214 described above. Namely, the data measurements may be performed at a first (fixed) sampling rate (e.g., $R_1$ or other rate value). Once the pattern associated with the process 302 is identified, the data measurements may be performed in a second measurement mode 316, which may comprise performing data measurements at a second sampling rate (e.g., $R_3$). The second sampling rate $R_3$ may be lower than the first sampling rate $R_1$, as shown in FIG. 3, and may be defined as the lowest possible rate, using which rate the predicted appearance of events 306, 308 of the process 302 may be verified.

Figure 4:
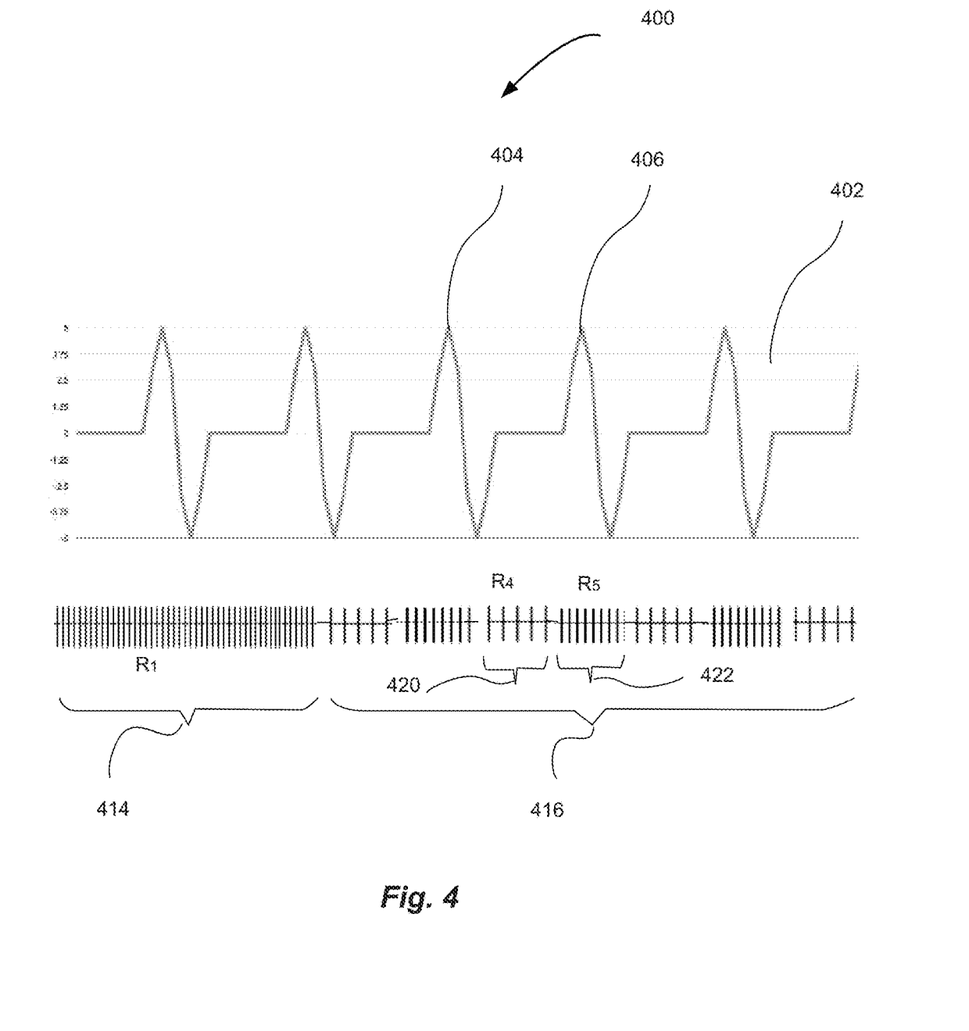
FIG. 4 is a schematic representation of another example predictive data measurement performance technique, using one or more sensors for data measurements of a process, according to some embodiments.

FIG. 4 is a schematic representation 400 of another example predictive data measurement performance technique, using one or more sensors for data measurements of a process, according to some embodiments. Similarly to the techniques described in reference to FIGS. 2 and 3, data measurements of a process 402 may be initially performed in a first data measurement mode 414, similar to 214 and/or 314 described above. Namely, the data measurements may be performed at a first (fixed) sampling rate (e.g., $R_1$ or other rate value).

Once the pattern associated with the process 402 is identified, the data measurements may be performed in a second measurement mode 416, which may comprise sub-modes 420 and 422, as shown in FIG. 4. In sub-mode 420, the data measurements may be performed at a second sampling rate $R_4$ during periods of time between predicted appearances of consecutive events (e.g., 404, 406, and so on) in the process 402. In the sub-mode 422, the data measurements may be performed at a third sampling rate $R_5$ during the periods of time corresponding to appearances of events (e.g., 404, 406, and so on). In some embodiments, the third sampling rate $R_5$ may be greater than the second sampling rate $R_4$. In other embodiments, the third sampling rate $R_5$ may be lower than the second sampling rate $R_4$. For example, the periods of time corresponding to appearances of events may be shorter than the periods of time between the appearances of events, and vice versa.

In addition to the techniques described in reference to FIGS. 2-4, other data measurement techniques may be contemplated. For example, a data measurement technique may be directed at reducing power consumption by the processor of a computing device engaged in processing measured data, such as the processor 132 of the computing device 102 of FIG. 1. In this example, the data measurements may be performed by one or more sensors in a first data measurement mode at a first sampling rate, the pattern of events may be determined, and a second data measurement mode may be initiated. The second data measurement mode may include, in this instance, continuing to perform data measurements by one or more sensors in the first data measurement mode (e.g., at the first sampling rate), and processing, by the processor, the data measurements that are taken during periods of time corresponding to the predicted appearance of events in the process, while refraining from processing the data measurements taken at other times.

In some embodiments, data measurements may be performed by multiple sensors. An example data measurement process directed at reducing power consumption by the multiple sensors may include performing the data measurements at a first sampling rate by the multiple sensors (e.g., in a first data measurement mode), determining the pattern of events, and switching to a second data measurement mode comprising performing the data measurements at the same first sampling rate by at least one of the multiple sensors and ceasing to perform the data measurements by at least another one of the multiple sensors. For example, just one sensor may perform data measurements in the second data measurement mode.

Figure 5:
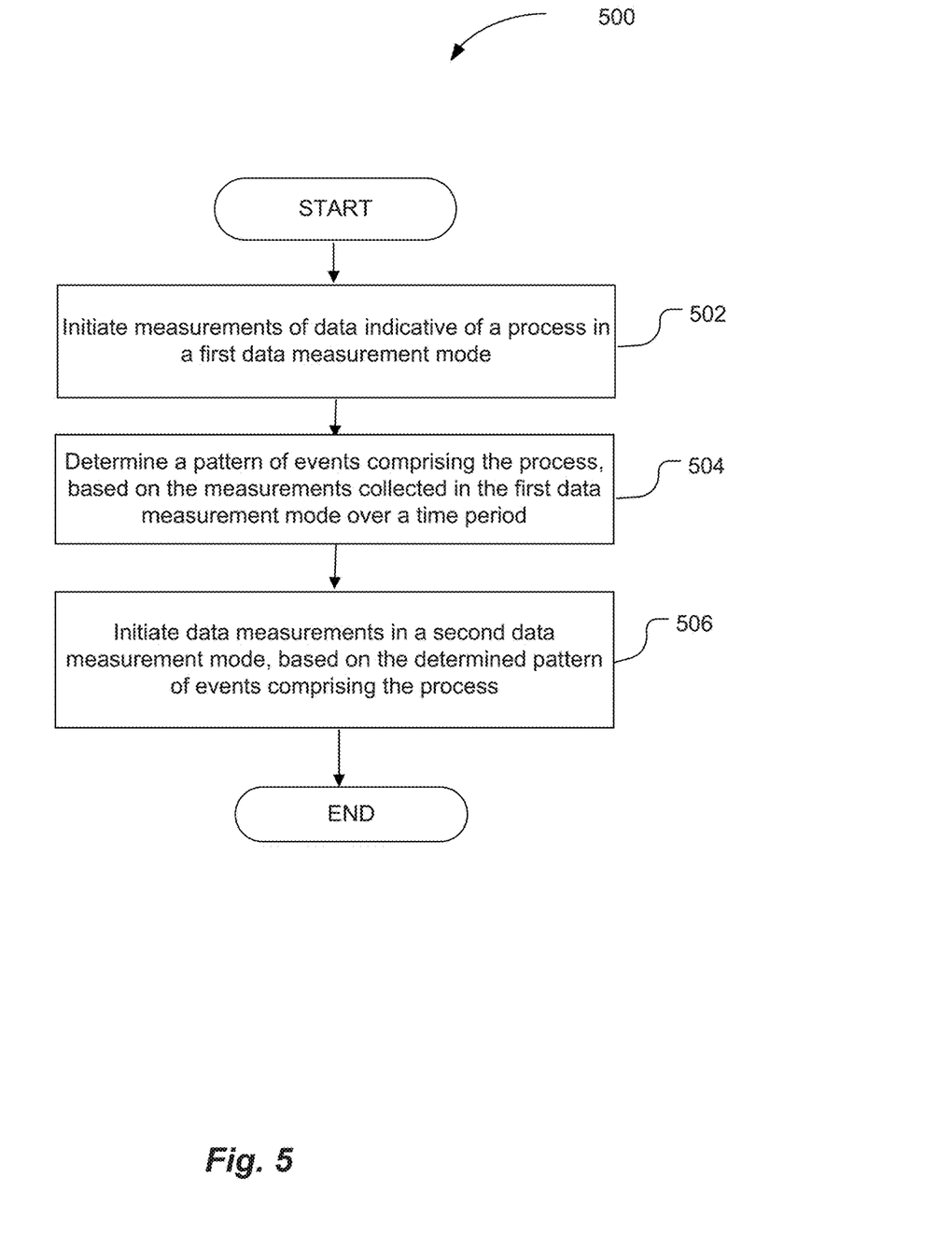
FIG. 5 is a process flow diagram for performing predictive data measurements by one or more sensors, in accordance with some embodiments.

FIG. 5 is a process flow diagram 500 for performing predictive data measurements by one or more sensors, in accordance with some embodiments. The process 500 may be performed, for example, by the sensor management module 150 and data processing module 146 of FIG. 1.

The process 500 may begin at block 502, wherein measurements of data indicative of a process (e.g., 202, 302, or 402) may be initiated in a first data measurement mode (e.g., 214, 314, or 414). To initiate the measurements, the sensor (or sensors) performing the measurements may, e.g., be powered on or reset.

At block 504, a pattern of events comprising the process may be determined, based on the measurements collected in the first data measurement mode over a time period.

At block 506, data measurements may be initiated in a second data measurement mode (e.g., 216, 316, 416, or others described above), based on the determined pattern of events comprising the process.

Figure 6:
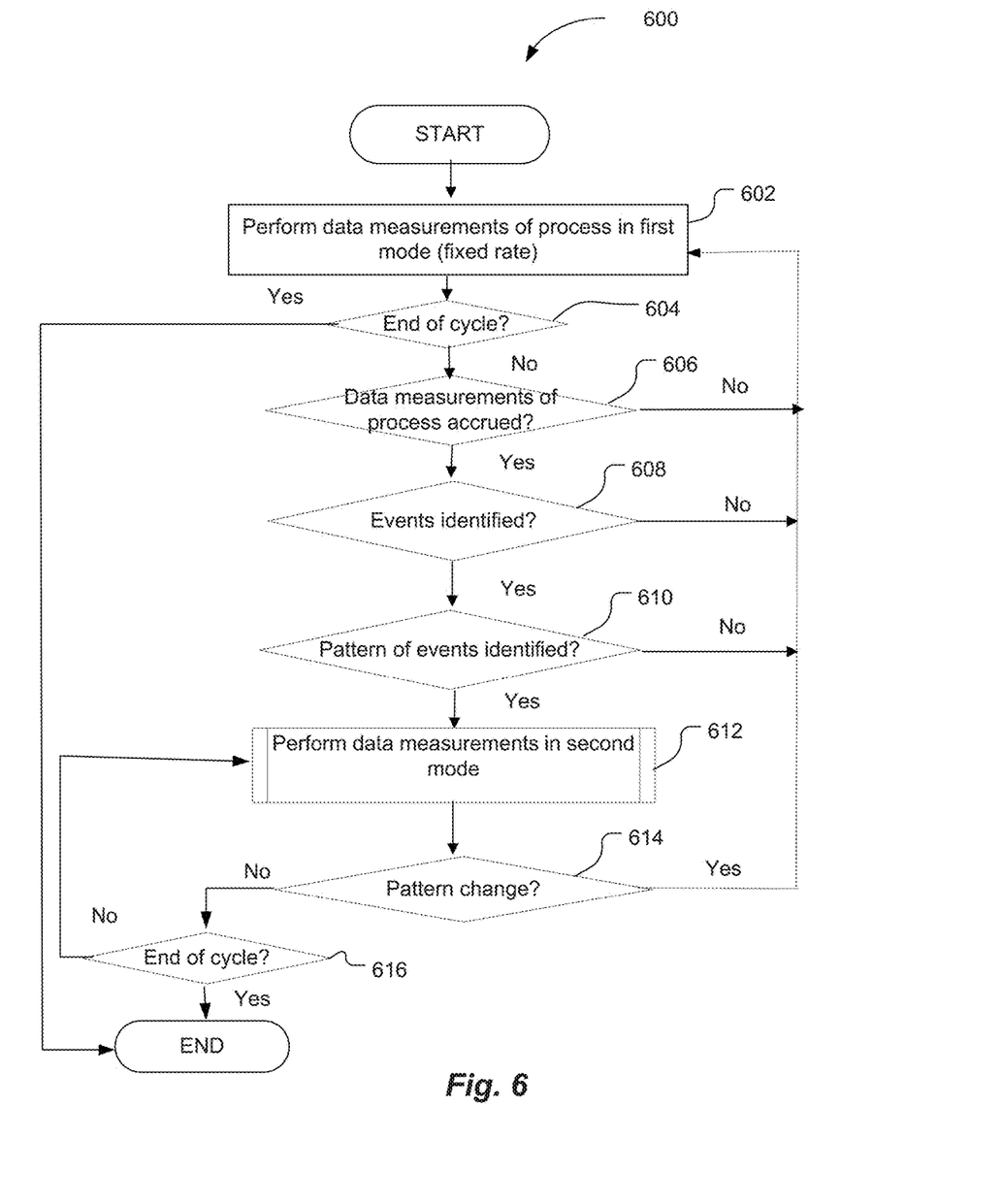
FIG. 6 is another process flow diagram for performing data measurements by one or more sensors, in accordance with some embodiments.

FIG. 6 is another process flow diagram 600 for performing data measurements by one or more sensors, in accordance with some embodiments. The process 600 elaborates on the process 500 in greater detail. The process 600 may be performed, for example, by the sensor management module 150 and data processing module 146 of the system 100 of FIG. 1. By way of example only, one may assume that the system 100 comprises a wearable device, such as a smart watch (e.g., Basis® smart watch) having a heart rate monitor.

The process 600 may begin at block 602, where data measurements of a process may be performed by one or more sensors in a first data measurement mode (e.g., at a fixed sampling rate), similar to the processes described in reference to FIGS. 2-4. Continuing with the smart watch example, a heart rate monitor may be turned on (powered on) to conduct the user's heart rate measurements in the first data measurement mode.

The data measurements may be scheduled to continue for a determined period of time (measurement cycle). For example, the smart watch heart rate monitor may be set to perform heart rate measurements for a particular period of time. Accordingly, at decision block 604, it may be determined whether the data measurement cycle is over. If the data measurement cycle is continuing, the process 600 may move to decision block 606.

At decision block 606, it may be determined whether the data measurements of the process have been accumulated since the beginning of the data measurement cycle. For example, sufficient sampling data may need to be collected in order to perform pattern determination described in reference to FIG. 2. If sufficient sampling data has not been accumulated, the process 600 may revert to block 602. Otherwise, the process 600 may move to decision block 608.

At decision block 608, it may be determined whether any events indicative of the process have been identified. Continuing with the smart watch example, the events may comprise heartbeats of the user's heart. However, the user may not necessarily wear the watch all the time. For example, if the watch is sitting on the user's desk, the heart monitor may be powered on, but no heartbeats may be sensed and identified as events. Accordingly, if no events have been identified, the process 600 may revert to block 602. Otherwise, the process 600 may move to decision block 610.

At decision block 610, it may be determined whether the pattern of events indicative of the process has been identified. Continuing with the smart watch example, if the watch is worn by the user, the heart rate may be determined over a certain period of time (e.g., one minute). More specifically, the heartbeats of particular amplitude and intervals between them may be identified.

Accordingly, if no events have been identified, the process 600 may revert to block 602. Otherwise, the process 600 may move to block (routine) 612, which provides for performing data measurements in a second data measurement mode. The second data measurement mode may include a number of different data measurement processes, some of which were described in reference to FIGS. 2-4. The routine 612 will be described in reference to FIG. 7 in greater detail.

During performance of data measurements in the second data measurement mode, it may be determined, at decision block 614, whether the pattern identified at decision block 612 has changed. More specifically, the measured events of the process may no longer match the identified pattern of events, which may be established during the data measurement performance in the second data measurement mode as described in reference to FIG. 2. Continuing with the smart watch example, the heart rate determined during the first data measurement mode may pertain to the user sleeping state. If the user woke up and, for example, started running, her heart rate may change (e.g., increase beyond a particular threshold) such that the sleeping state heart rate-related pattern may no longer be correct.

Accordingly, if the pattern has changed, the process 600 may revert to block 602, to resume performing the data measurements in the first data measurement mode in order to identify a new pattern of events, if any (e.g., determine new heart rate pattern related to the user's running state, following the smart watch example). If the pattern has not changed, the process 600 may move to decision block 616, where the check for the end of the measurement cycle may be performed. If the measurement cycle has ended, the process 600 ends. Otherwise, the data measurements continue in the second data measurement mode, as indicated by block 612.

Figure 7:
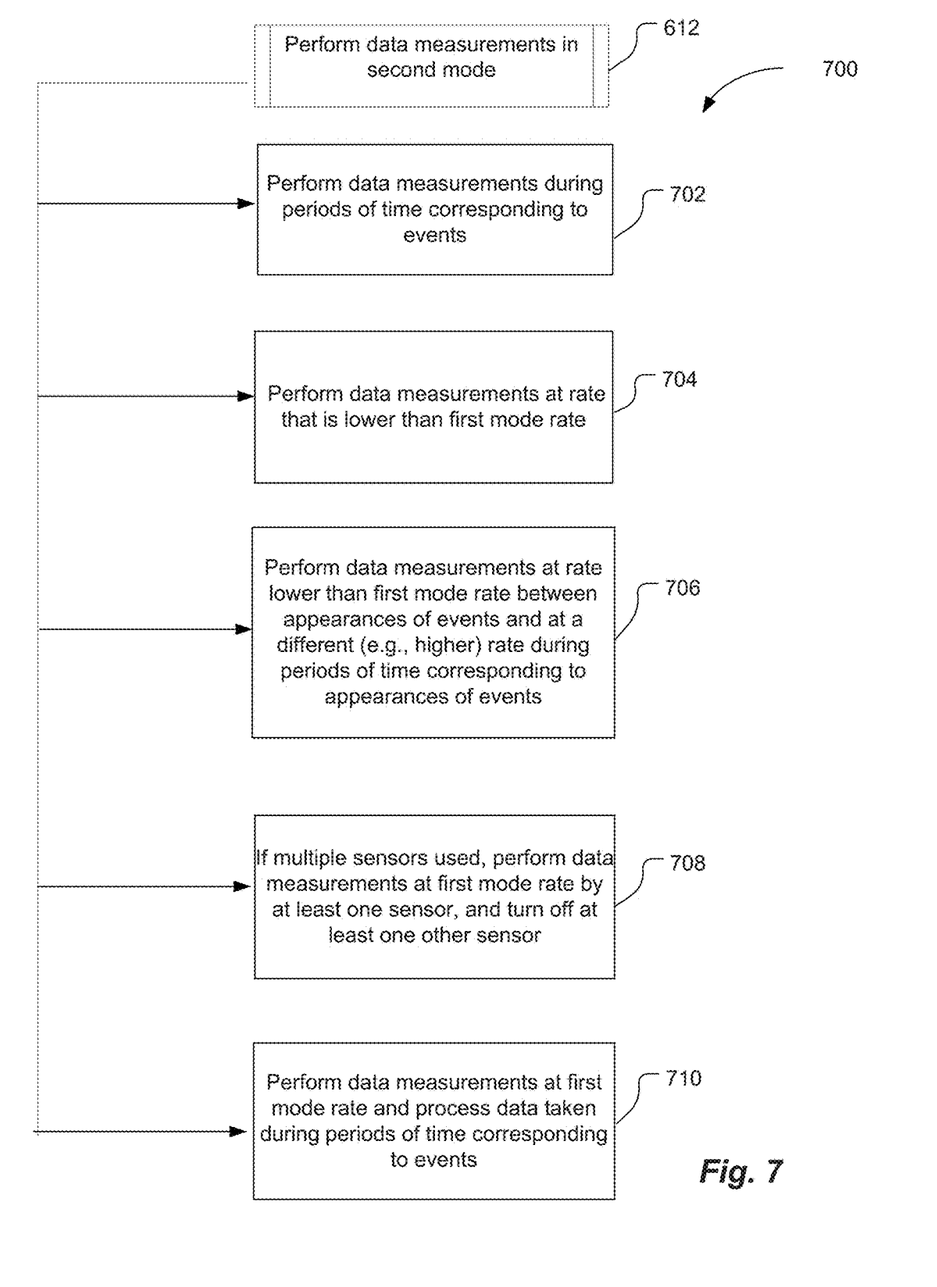
FIG. 7 is a block diagram illustrating different examples of performing data measurements in the second data measurement mode described in reference to FIGS. 2-6, according to some embodiments.

FIG. 7 is a block diagram 700 illustrating different examples of performing data measurements in the second data measurement mode, according to some embodiments. The block diagram 700 provides at least some implementations of routine 612 described in reference to FIG. 6.

As shown, routine 612 "Perform data measurements in the second data measurement mode" may include, but is not limited to, at least one of the processes indicated by blocks 702, 704, 706, 708, or 710.

Block 702 may include the process described in reference to FIG. 2. Namely, the process of block 702 may include performing data measurements during periods of time corresponding to the appearance of events in the process, as determined by the pattern of events identified during performance of data measurements in the first data measurement mode.

Block 704 may include the process described in reference to FIG. 3. Namely, the process of block 704 may include performing data measurements at a sampling rate that is lower than the rate associated with the first data measurement mode.

Block 706 may include the process described in reference to FIG. 4. Namely, the process of block 706 may include performing data measurements at a sampling rate that is lower than the first data measurement mode rate between appearances of events, and at a different (e.g., higher) rate during periods of time corresponding to appearances of the events.

Block 708 may include the process configured to reduce power consumption in the case of multiple sensors performing data measurements. Namely, the number of sensors performing the data measurements at least in the first data measurement mode may be reduced. For example, in the second data measurement mode, one sensor may perform data measurements (e.g., continue to perform measurements at a rate corresponding to the first data measurement mode) and other sensors may be turned off or switch to another measurement mode, similar to the second measurement mode described in reference to blocks 702, 704, or 706.

In general, at least one sensor may perform measurements at the first mode rate, and at least one other sensor may be turned off (powered off) or switch to a different measurement mode. For example, in some embodiments, one sensor may be run in the first data measurement mode, while other sensor(s) may be run in the second measurement mode. For example, an accelerometer and optical sensor may both be necessary to determine heart rate. Once the heart rate pattern is determined, the accelerometer may run continuously in the first measurement mode while the optical sensor may run in a second measurement mode.

Block 710 may include the process configured to reduce power consumption by the processor 132 of the computing device 102 described in reference to FIG. 1. For example, data measurements may continue to be performed at a sampling rate corresponding to the first data measurement mode. The data measured only during periods of time corresponding to the appearance of events in the process may be processed by the processor 132, e.g., using the data processing module 146, thus reducing the total amount of data processed by the processor 132.

In another embodiment, some portion of the sensor data may be buffered in memory 134. If the pattern is detected to have changed, the processor 132 may retrospectively reprocess the buffered data rather than waiting for new sensor samples to be collected. This may avoid having to wait for more sensor data to come in if the pattern changes.

Figure 8:
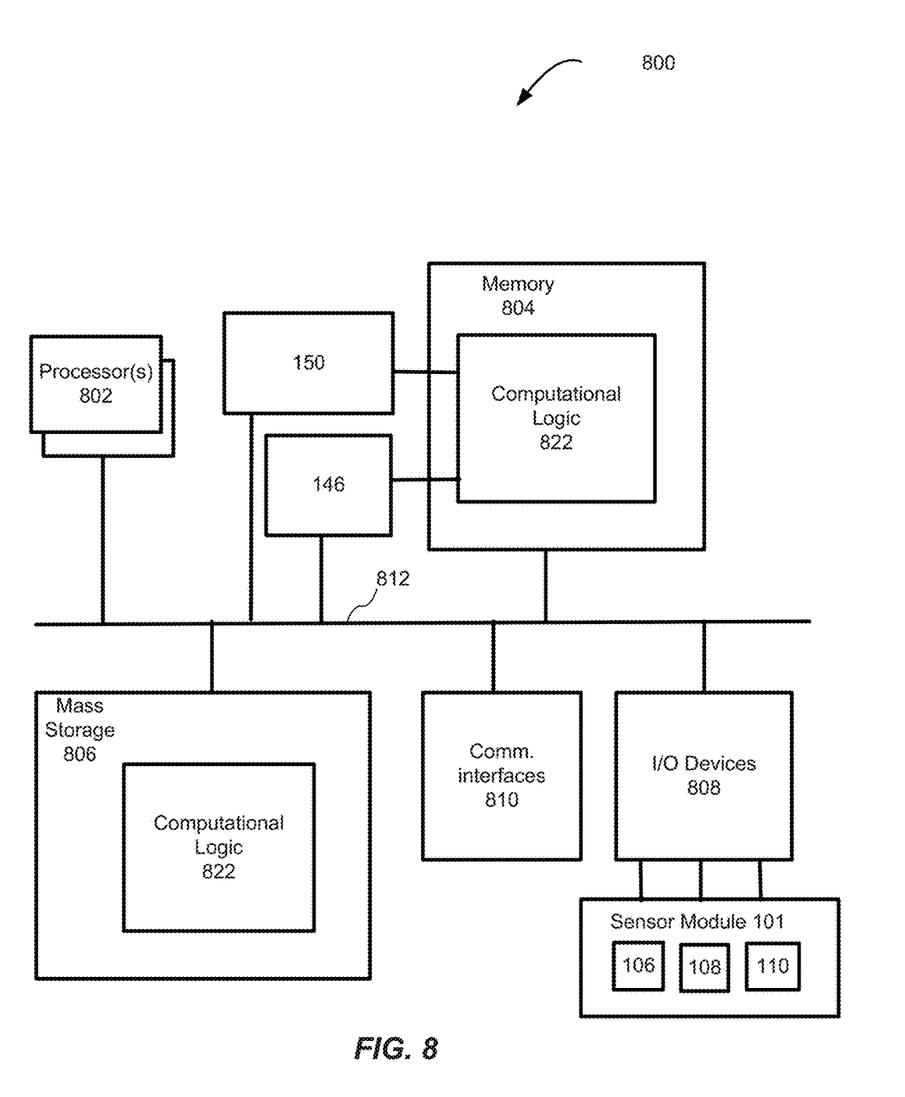
FIG. 8 illustrates an example computing device suitable for use with various components of FIG. 1, such as a computing device configured to operate the sensor module, in accordance with various embodiments.

FIG. 8 illustrates an example computing device 800 suitable for use with various components of FIG. 1, such as computing device 102 configured to operate the sensor module 101 of FIG. 1, in accordance with various embodiments. As shown, computing device 800 may include one or more processors or processor cores 802 and system memory 804. For the purpose of this application, including the claims, the terms "processor" and "processor cores" may be considered synonymous, unless the context clearly requires otherwise. The processor 802 may include any type of processors, such as a central processing unit (CPU), a microprocessor, and the like. The processor 802 may be implemented as an integrated circuit having multi-cores, e.g., a multi-core microprocessor. The computing device 800 may include mass storage devices 806 (such as diskette, hard drive, volatile memory (e.g., dynamic random-access memory (DRAM), compact disc read-only memory (CD-ROM), digital versatile disk (DVD), and so forth). In general, system memory 804 and/or mass storage devices 806 may be temporal and/or persistent storage of any type, including, but not limited to, volatile and non-volatile memory, optical, magnetic, and/or solid state mass storage, and so forth. Volatile memory may include, but is not limited to, static and/or dynamic random-access memory. Non-volatile memory may include, but is not limited to, electrically erasable programmable read-only memory, phase change memory, resistive memory, and so forth.

The computing device 800 may further include input/output (I/O) devices 808 (such as a display), keyboard, cursor control, remote control, gaming controller, image capture device, and so forth) and communication interfaces 810 (such as network interface cards, modems, infrared receivers, radio receivers (e.g., Bluetooth), and so forth).

The communication interfaces 810 may include communication chips (not shown) that may be configured to operate the device 800 in accordance with a Global System for Mobile Communication (GSM), General Packet Radio Service (GPRS), Universal Mobile Telecommunications System (UMTS), High Speed Packet Access (HSPA), Evolved HSPA (E-HSPA), or Long-Term Evolution (LTE) network. The communication chips may also be configured to operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). The communication chips may be configured to operate in accordance with Code Division Multiple Access (CDMA), Time Division Multiple Access (TDMA), Digital Enhanced Cordless Telecommunications (DECT), Evolution-Data Optimized (EV-DO), derivatives thereof, as well as any other wireless protocols that are designated as 3G, 4G, 5G, and beyond. The communication interfaces 810 may operate in accordance with other wireless protocols in other embodiments.

The above-described computing device 800 elements may be coupled to each other via system bus 812, which may represent one or more buses. In the case of multiple buses, they may be bridged by one or more bus bridges (not shown). Each of these elements may perform its conventional functions known in the art. In particular, system memory 804 and mass storage devices 806 may be employed to store a working copy and a permanent copy of the programming instructions implementing the operations described in reference to the sensor management module 150 of FIG. 1. The various elements may be implemented by assembler instructions supported by processor(s) 802 or high-level languages that may be compiled into such instructions.

The permanent copy of the programming instructions may be placed into permanent storage devices 806 in the factory, or in the field, through, for example, a distribution medium (not shown), such as a compact disc (CD), or through communication interface 810 (from a distribution server (not shown)). That is, one or more distribution media having an implementation of the agent program may be employed to distribute the agent and to program various computing devices.

The number, capability, and/or capacity of the elements 808, 810, 812 may vary, depending on whether computing device 800 is used as a stationary computing device, such as a set-top box or desktop computer, or a mobile computing device, such as a wearable device, tablet computing device, laptop computer, game console, or smartphone. Their constitutions are otherwise known, and accordingly will not be further described.

At least one of processors 802 may be packaged together with computational logic 822 configured to practice aspects of embodiments described in reference to FIGS. 1-7. For one embodiment, at least one of processors 802 may be packaged together with computational logic 822 configured to practice aspects of sensor management and data processing to form a System in Package (SiP) or a System on Chip (SoC). For at least one embodiment, the SoC may be utilized in, e.g., but not limited to, a mobile computing device such as a computing wearable device, tablet, or smartphone. For example, computational logic 822 may be associated with, or otherwise configured to include or access, sensor management module 150 and data processing module 146 similar to ones described in reference to FIG. 1.

The computing device 800 may include or otherwise be associated with a sensor module, such as sensor module 101 having sensors 106, 108, 110, for performing process data measurements according to the embodiments described above. In some embodiments, the sensor module 101 may be communicatively coupled with the computing device 800 as described in reference to FIG. 1. For example, the sensor module 101 may be coupled with, or otherwise be associated with, I/O devices 808.

In various implementations, the computing device 800 may comprise a laptop, a netbook, a notebook, an ultrabook, a smartphone, a tablet, a personal digital assistant (PDA), an ultra mobile PC, a mobile phone, or a digital camera. In further implementations, the computing device 800 may be any other electronic device that processes data.

The embodiments described herein may be further illustrated by the following examples. Example 1 is an apparatus for predictive data measurement, comprising: one or more sensors; and a sensor management module coupled with the one or more sensors, wherein the sensor management module is to: initiate measurements of data indicative of a process, by the one or more sensors in a first data measurement mode; determine a pattern of events comprising the process, based on a portion of the measurements collected by the one or more sensors in the first data measurement mode over a time period, wherein the pattern is to indicate a prediction of appearance of events in the process; and initiate measurements of the data by the one or more sensors in a second data measurement mode, wherein the second mode is based on the pattern of events comprising the process.

Example 2 may include the subject matter of Example 1, and further specifies that the sensor management module is to: determine, from the data being measured in the second data measurement mode, that a match of the events to the pattern is above a margin of error; and revert to the first data measurement mode of data measurements in response to the determine that a match of the events to the pattern is above a margin of error.

Example 3 may include the subject matter of Example 1, and further specifies that the one or more sensors are selected from one or more of: an accelerometer, a gyroscope, a barometer, an infrared proximity sensor, a visible light sensor, microphone, compass, thermometer, moisture sensor, or a biometric sensor.

Example 4 may include the subject matter of Example 1, and further specifies that the apparatus of claim 1, wherein to initiate the data measurements in the first data measurement mode comprises to perform the data measurements at a first sampling rate.

Example 5 may include the subject matter of Example 4, and further specifies that to initiate the data measurements in the second data measurement mode comprises to: perform the data measurements at a second sampling rate that is lower than the first sampling rate; perform the data measurements at a third sampling rate during first periods of time corresponding to predicted appearances of events according to the determined pattern; or perform the data measurements at a fourth sampling rate during second periods of time between predicted appearances of consecutive events in the process and to perform the data measurements at a fifth sampling rate during the first periods of time, wherein the fifth sampling rate is different than the fourth sampling rate.

Example 6 may include the subject matter of Example 5, and further specifies that the fourth sampling rate is equal to or lower than the first sampling rate.

Example 7 may include the subject matter of Example 5, and further specifies that to determine a pattern of events comprising the process includes to identify data points and time instances approximately at which the identified data points are to be measured by the one or more sensors, wherein the measured data points match the identified data points within a desired margin of error.

Example 8 may include the subject matter of Example 7, and further specifies that the time instances are within the first time period.

Example 9 may include the subject matter of Example 1, and further specifies that the one or more sensors comprise multiple sensors, wherein the first data measurement mode comprises to perform the data measurements at a first sampling rate by the multiple sensors, and wherein the second data measurement mode comprises: to perform the data measurements at the first sampling rate by at least one of the multiple sensors and cease to perform the data measurements by at least another one of the multiple sensors, or to perform the data measurements at the first sampling rate by at least one of the multiple sensors and perform the data measurements at the second sampling rate by at least another one of the multiple sensors.

Example 10 may include the subject matter of Example 1, and further specifies that the apparatus may further comprise a data processing module coupled with the one or more sensors to process the data measurements, wherein the first and second data measurement modes comprise to perform the data measurements at a first sampling rate, wherein the data processing module is to process the data measurements by the one or more sensors that are taken during periods of time corresponding to the predicted appearance of events in the process.

Example 11 may include the subject matter of Examples 1 to 10, and further specifies that to initiate data measurements by the one or more sensors in a first data measurement mode includes to power on one or more sensors.

Example 12 is a computer-implemented method for predictive data measurement, comprising: initiating, by a computing device, measurements of data indicative of a process by one or more sensors, in a first data measurement mode; determining, by the computing device, a pattern of events comprising the process, based on a portion of the measurements collected by the one or more sensors in the first data measurement mode over a time period, wherein the pattern indicates a prediction of appearance of events in the process; and initiating, by the computing device, measurements of the data by the one or more sensors in a second data measurement mode, wherein the second mode is based on the pattern of events comprising the process.

Example 13 may include the subject matter of Example 12, and further specifies that the method may include determining, by the computing device, from the data measured in the second mode, that a match of the events to the pattern is above a margin of error; and reverting, by the computing device, to the first data measurement mode of data measurements in response to determining that a match of the events to the pattern is above a margin of error.

Example 14 may include the subject matter of Example 12, and further specifies that initiating measurements in a first data measurement mode includes causing the one or more sensors to perform the data measurements at a first sampling rate.

Example 15 may include the subject matter of Example 14, and further specifies that initiating measurements of the data by the one or more sensors in a second data measurement mode includes one of: causing, by the computing device, performance of the data measurements at a second sampling rate that is lower than the first sampling rate; causing, by the computing device, performance of the data measurements at a third sampling rate during first periods of time corresponding to predicted appearances of events according to the determined pattern; or causing, by the computing device, performance of the data measurements at a fourth sampling rate during second periods of time between predicted appearances of consecutive events in the process, and performance of the data measurements at a fifth sampling rate during the first periods of time, wherein the fifth sampling rate is different than the fourth sampling rate.

Example 16 may include the subject matter of Examples 12 to 15, and further specifies that the events include appearance of data values within a predicted data range that are measured by the one or more sensors approximately at a predicted time of appearance of the data values, according to the determined pattern.

Example 17 is a non-transient computing device-readable storage medium having instructions for predictive data measurement that, in response to execution on a computing device, cause the computing device to: initiate measurements of data indicative of a process by one or more sensors accessible by the computing device, in a first data measurement mode; determine a pattern of events comprising the process, based on a portion of the measurements collected by the one or more sensors in the first data measurement mode over a time period, wherein the pattern indicates a prediction of appearance of events in the process; and initiate measurements of the data by the one or more sensors in a second data measurement mode, wherein the second mode is based on the pattern of events comprising the process.

Example 18 may include the subject matter of Example 17, and further specifies that the instructions, in response to execution on the computing device, further cause the computing device to: determine, from the data being measured in the second mode, that a match of the events to the pattern is above a margin of error; and revert to the first data measurement mode of data measurements, in response to a determination that a match of the events to the pattern is above a margin of error.

Example 19 may include the subject matter of Examples 17 to 18, and further specifies that to initiate the data measurements in the first data measurement mode comprises to perform the data measurements at a first sampling rate.

Example 20 may include the subject matter of Example 19, and further specifies that to initiate the data measurements in the second data measurement mode comprises to: perform the data measurements at a second sampling rate that is lower than the first sampling rate; perform the data measurements at a third sampling rate during first periods of time corresponding to predicted appearances of events according to the determined pattern; or perform the data measurements at a fourth sampling rate during second periods of time between predicted appearances of consecutive events in the process and to perform the data measurements at a fifth sampling rate during the first periods of time, wherein the fifth sampling rate is different than the fourth sampling rate.

Example 21 is an apparatus for predictive data measurement, comprising: means for initiating measurements of data indicative of a process by one or more sensors accessible by the computing device, in a first data measurement mode; means for determining a pattern of events comprising the process, based on a portion of the measurements collected by the one or more sensors in the first data measurement mode over a time period, wherein the pattern indicates a prediction of appearance of events in the process; and means for initiating measurements of the data by the one or more sensors in a second data measurement mode, wherein the second mode is based on the pattern of events comprising the process.

Example 22 may include the subject matter of Example 21, and further specifies that means for determining, from the data being measured in the second mode, that a match of the events to the pattern is above a margin of error; and means for reverting to the first data measurement mode of data measurements, in response to a determination that a match of the events to the pattern is above a margin of error.

Example 23 may include the subject matter of Examples 21 to 22, and further specifies that the means for initiating measurements in a first data measurement mode comprise means for performing the data measurements at a first sampling rate.

Example 24 may include the subject matter of Example 23, and further specifies that the means for initiating the data measurements in the second data measurement mode comprises: means for performing the data measurements at a second sampling rate that is lower than the first sampling rate; means for performing the data measurements at a third sampling rate during first periods of time corresponding to predicted appearances of events according to the determined pattern; or means for performing the data measurements at a fourth sampling rate during second periods of time between predicted appearances of consecutive events in the process and performing the data measurements at a fifth sampling rate during the first periods of time, wherein the fifth sampling rate is different than the fourth sampling rate.

Various operations are described as multiple discrete operations in turn, in a manner that is most helpful in understanding the claimed subject matter. However, the order of description should not be construed as to imply that these operations are necessarily order dependent. Embodiments of the present disclosure may be implemented into a system using any suitable hardware and/or software to configure as desired.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims and the equivalents thereof.

What is claimed is:

1. An apparatus for collecting measurements of a process, comprising:
   a sensor circuitry including one or more sensors, to collect measurements of the process;
   a power source coupled with the sensor circuitry to supply power to the one or more sensors; and
   one or more sensor management and data processing modules coupled with the sensor circuitry, to regulate the power source in supplying power to the one or more sensors and operation of the one or more sensors, which includes to:
   operate the power source to power on the one or more sensors, to measure the process at a first sampling rate, in a first data measurement mode, over a time period;
   determine a pattern of events making up the process, based on the measurements collected by the one or more sensors in the first data measurement mode over the time period, wherein to determine the pattern of events includes to identify data points of the process and time intervals during which the data points are to be measured by the one or more sensors, wherein the pattern includes appearance of the identified data points in the identified time intervals;
   operate the power source to power on the one or more sensors to measure the process in a second data measurement mode, which includes to measure the data points at a second sampling rate during the identified time intervals, and refrain from the measurements at the first sampling rate between the identified time intervals, wherein the second sampling rate is different than the first sampling rate.

2. The apparatus of claim 1, wherein the one or more sensors are selected from:
   an accelerometer, a gyroscope, a barometer, an infrared proximity sensor, a visible light sensor, a microphone, a compass, a thermometer, a moisture sensor, or a biometric sensor.

3. The apparatus of claim 1, wherein the second sampling rate is lower than the first sampling rate.

4. The apparatus of claim 1, wherein the measured data points match the identified data points within a margin of error.

5. The apparatus of claim 1, wherein the one or more sensor management and data processing modules are to determine, from the data measured in the second data measurement mode, that a match of the measured data points to the identified data points is above a margin of error; and revert to the first data measurement mode of data measurements.

6. The apparatus of claim 1, wherein the one or more sensors comprise multiple sensors, wherein to measure the process in the first data measurement mode comprises to perform the measurements at the first sampling rate by the multiple sensors, and wherein the second data measurement mode comprises:
   to perform the measurements by at least one of the multiple sensors and cease to perform the measurements by at least another one of the multiple sensors, or
   to perform the measurements at the second sampling rate by at least one of the multiple sensors and perform the measurements at a third sampling rate by at least another one of the multiple sensors.

7. The apparatus of claim 1, wherein the one or more sensor management and data processing modules is to process the measurements of the process.

8. A computer-implemented method, comprising:
   operating, by a computing device of a system, a power source coupled with a sensor circuitry of the system, to power on one or more sensors of the system, to cause the one or more sensors to perform measurements of a process in a first data measurement mode, at a first sampling rate, over a first time period;

determining, by the computing device, a pattern of events making up the process, based on the measurements collected by the one or more sensors in the first data measurement mode over the first time period, including identifying data points of the process and time intervals during which the data points are to be measured by the one or more sensors, wherein the pattern includes appearance of the identified data points in the identified time interval; and operating, by the computing device, the power source to power on the one or more sensors to measure the process in a second data measurement mode, including measuring the data points at a second sampling rate during the identified time intervals, and refraining from the measurements at the first sampling rate between the identified time intervals, wherein the second sampling rate is different than the first sampling rate.

9. The computer-implemented method of claim 8, further comprising:

determining, by the computing device, from the data measured in the second data measurement mode, that a match of the measured data points to the identified data points is above a margin of error; and reverting, by the computing device, to the measurements in the first data measurement mode.

10. The computer-implemented method of claim 8, wherein the second sampling rate is lower than the first sampling rate.

11. A non-transient computing device-readable storage medium having instructions that, in response to execution on a computing device of a system, cause the computing device to:

operate a power source coupled with a sensor circuitry of the system, to power on one or more sensors of the system, to cause the one or more sensors to perform measurements of a process, in a first data measurement mode, which includes a periodic performance of the measurements of the process at a first sampling rate, over a time period;

determine a pattern of events making up the process, based on the measurements collected by the one or more sensors in the first data measurement mode over the time period, wherein to determine the pattern of events includes to identify data points of the process and time intervals during which the data points are to be measured by the one or more sensors, wherein the pattern includes appearance of the identified data points in the identified time intervals; and operate the power source to power on the one or more sensors to measure the process in a second data measurement mode, which includes to measure data points at a second sampling rate during the identified time intervals, and refrain from performance of the measurements at the first sampling rate between the identified time intervals, wherein the second sampling rate is different than the first sampling rate.

12. The non-transient computing device-readable storage medium of claim 11, wherein the instructions, in response to execution on the computing device, further cause the computing device to:

determine, from the data being measured in the second data measurement mode, that a match of the events to the pattern is above a margin of error; and revert to the first data measurement mode of data measurements.

13. The non-transient computing device-readable storage medium of claim 11, wherein the second sampling rate is lower than the first sampling rate.

* * * * *